United States Patent [19]
Boyd, Sr.

[11] Patent Number: 5,513,656
[45] Date of Patent: May 7, 1996

[54] INTRAORAL SEMI-CUSTOM DISCLUDER DEVICE

[76] Inventor: James P. Boyd, Sr., 71 E. Long Lake, Bloomfield Hills, Mich. 48302

[21] Appl. No.: 410,978

[22] Filed: Mar. 27, 1995

[51] Int. Cl.$^6$ .................................................. A61C 5/14
[52] U.S. Cl. ............................................. 128/859; 433/6
[58] Field of Search .................................. 128/859, 861, 128/862, 857, 848, 846; 602/902; 433/6

[56] References Cited

U.S. PATENT DOCUMENTS

| | | | |
|---|---|---|---|
| 2,694,397 | 11/1954 | Herms | 128/861 |
| 2,808,898 | 7/1957 | Greenblum | 128/861 |
| 3,478,429 | 11/1969 | Shilliday | 433/6 |
| 4,559,013 | 12/1985 | Amstutz et al. | 433/6 |
| 4,773,853 | 9/1988 | Kussids | 433/6 |
| 5,033,480 | 7/1991 | Wiley et al. | 128/861 |
| 5,067,896 | 11/1991 | Korn | 433/6 |
| 5,092,346 | 11/1992 | Hays et al. | 128/848 |
| 5,277,203 | 1/1994 | Hays | 128/861 |

FOREIGN PATENT DOCUMENTS

| | | | |
|---|---|---|---|
| 2945046 | 1/1981 | Germany | 128/861 |

*Primary Examiner*—Jessica J. Harrison
*Assistant Examiner*—Michael O'Neill
*Attorney, Agent, or Firm*—John R. Duncan; Frank D. Gilliam

[57] ABSTRACT

An intraoral semi-custom device for the prevention of chronic tension and common migraine headaches and temporomandibular disorders that are caused by chronic clenching of the posterior mandibular and maxillary teeth by the temporalis muscle. The semi-custom discluder is a small intraoral device which is obtained and modified by an individual wearer. The device includes a trough, curved to correspond to the curvature of the maxillary incisors, from which distally extends a dome shape. The trough is retained by a resilient material, usually silicone, which is placed into the trough by the wearer and then placed over the maxillary incisors by the wearer. The cured silicone acts as a gasket and retains the device around the wearer's upper incisors. Once in place and the wearer their mouth, the dome will come into contact with one or two lower incisor teeth prior to the posterior teeth coming into contact. This renders the temporalis muscles ineffective, preventing high pressure clenching of the posterior teeth, thus preventing tension headache, commom migraine, and temporomandibular disorders. The dome can be modified by the wearer with extension tabs in the event the posterior teeth come into contact with each other prior to the lower incisors contacting the dome.

3 Claims, 1 Drawing Sheet

INTRAORAL SEMI-CUSTOM DISCLUDER DEVICE

BACKGROUND OF THE INVENTION

This invention relates in general to the prevention of tension and common migraine headaches and temporomandibular syndrome and, more specifically, to an intraoral, semi-custom device for preventing those conditions.

Many people suffer from recurring tension, or muscle contraction, headaches ranging from mild to severe. The severity of the headache often mimics the severity of classic migraine and can be diagnosed as "common migraine".

Tension is a muscular property. Muscles tense, or contract to do work. When a muscle contracts statically and continually it will become painful. The intensity or degree of contraction and longevity of contraction will dictate the degree of discomfort.

The majority of the muscles that cover the human head (i.e., skull) are responsible for facial expression (raising eyebrows, etc). These muscles are not strong enough to elicit the type of discomfort associated with headaches. There is an extremely powerful muscle, however, located on the side of the skull, extending from just behind the eye to just behind the ear. This muscle, the temporalis muscle, has one function, to close (or "elevate") the lower jaw. When isometrically contracted, the temporalis muscle can exert a tremendous amount of static force. This isometric contraction can only occur when the posterior mandibular and maxillary teeth or dentures are in contact with each other.

The common tension headache in the temporal region is caused by moderate to severe inappropriate contraction of the temporalis muscles. Under usual and normal circumstances, the upper and lower teeth should rarely, if ever, come in pressure contact other than during normal chewing. The inappropriate muscular activity that clenches the upper and lower jaws together along with their associated dentition is called myofascial dysfunction.

Clenching is a motionless act, therefore, it is practically impossibly to notice another person clenching. Additionally, clenching is most commonly done while the person is concentrating on another topic, or while dreaming, so that it is very difficult to have a self awareness of clenching.

As the muscular contraction condition of clenching continues, the muscles become fatigued and susceptible to spasm and cramping. The pain from spasming temporalis fibers is quite severe and is usually diagnosed as common migraine. This type os migraine initiates as a severe headache that may last for two to three days. The muscle contraction headache patient, when seen by a physician, is usually treated with muscle relaxants and analgesics and may be referred to a physical therapist to treat the fatigued muscles. However, this treats the symptoms but does not address the cause.

These patients, when seen by a dentist, are commonly diagnosed as having temporomandibular disorder. These patients are typically treated with an intraoral "jaw-positioning" appliance. Typical of these are the orthotics or splints described by Norton in U.S. Pat. No. 4,671,766 and Sullivan in U.S. Pat. No. 4,519,386. The appliance, or splint, covers either the upper or lower posterior teeth. Unfortunately, the upper and lower jaws are approximated by way of the splint, thus allowing the clenching to persist, and in many cases, intensify.

The applicant's prior patent (Boyd, U.S. Pat. No. 5,085,584) describes a device that does prevent clenching. Unfortunately for the sufferer, the device must be custom fabricated for each individual patient by a dentist, usually at a prohibitive cost (several hundred dollars) to the majority of sufferers.

Thus, there is continuing need for simplifing and improving means and methods for the prevention of clenching and the resultant headaches, at a reasonable cost to the sufferer, without having to seek professional service.

SUMMARY OF THE INVENTION

The above-noted problems, and others, are overcome in accordance with this invention by a small intraoral, semi-custom device that can be self-fitted in a person's mouth without the services and expense of a dentist. The device inhibits inappropriate isometric contraction of the temporalis muscles. The device includes a prefabricated trough, curved to correspond to the general curvature of the four anterior maxillary incisors. The trough is retained on the teeth by the placement of a silicone or soft resin within the trough which when placed over the teeth forms a sealing gasket, which then retains the trough on the teeth. Extending distally from the trough is a small dome shape that extends such that as the jaws come together, the lower (mandibular) anterior incisal teeth edges come into contact with the dome prior to the upper and lower posterior teeth coming into contact. This maintains the separation, or disclusion, of the posterior teeth and prevents clenching. The dome can be modified by the wearer so that disclusion is maintained in all mandibular excursive movements.

The device must be removed by the wearer when eating. The device can be installed at all other times, in particular, during stressful occasions and when sleeping.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
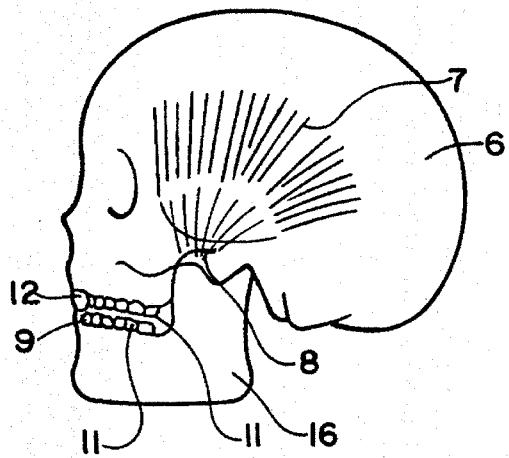
FIG. 1 is a schematic side view elevation of the human skull with the semi-custom discluder device of this invention in use.

Referring now to FIG. 1, there is seen a schematic representation of a human skull 6. The temporalis muscle 7 extends from the skull to it's attachment 8 on the mandible (jaw) 16, with contraction of the muscle 7 causing the jaw 16 to close. When the semi-custom discluder 12 of this invention (as detailed in FIGS. 2–4) is in place along the anterior maxillary teeth 10 in FIG. 1 and FIG. 5, only the anterior portion and perhaps the dome 13 is seen. As is apparent, the lower anterior teeth 9 contact the dome 13, preventing posterior teeth 11 from coming into contact.

Figure 2:
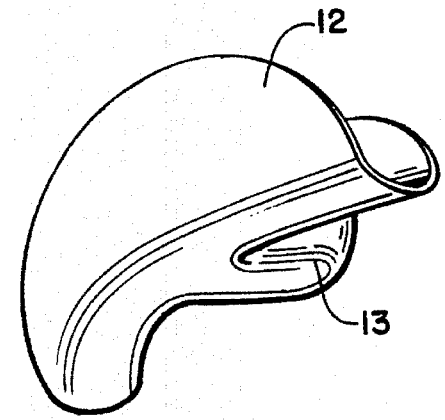
FIG. 2 is a perspective view of the semi-custom discluder device seen from the left-front-inferior.
Figure 3:
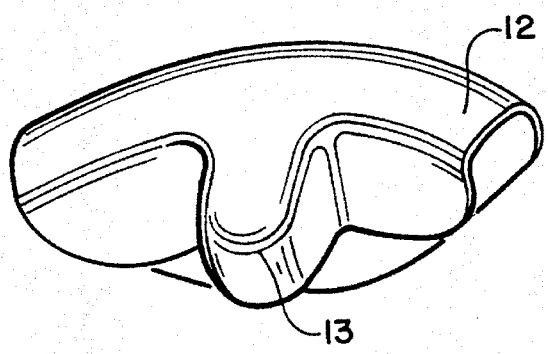
FIG. 3 is a perspective view of the semi-custom discluder device seen from the inferior-posterior.
Figure 4:
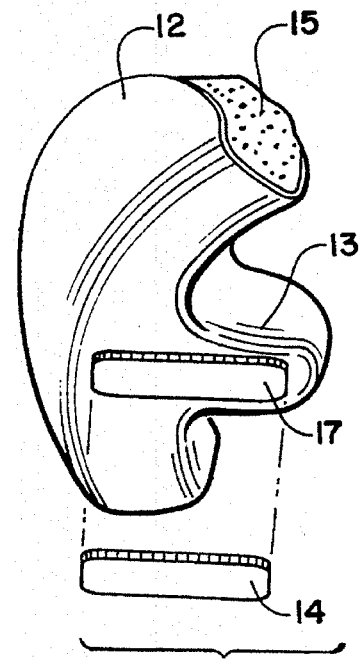
FIG. 4 is a perspective view of the semi-custom discluder device seen from the left-front-inferior, with the trough filled with silicon resin and with onr extending tab in place, and another extension tab aligned for placement.
Figure 5:
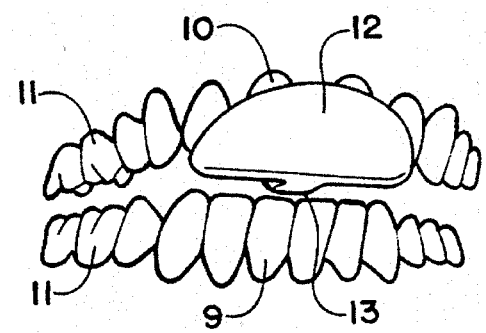
FIG. 5 is an anterior view of the semi-custom discluder device in function, secured onto the anterior maxillary incisors with the discluding dome opposing the mandibular incisors.

The semi-custom discluder 12 is shown in detail in FIGS. 2–4, which is a curved trough, similar to the curvature of the maxillary anterior teeth 10. Extending distally from the trough, is a dome 13, which the lower anterior incisors 9 come into contact with as the mandible 16 elevates. The semi-custom discluder 12 in held in place on the anterior maxillary incisors 10 by a resiliant material 15, such as silicone resin, placed within the trough 12 by the wearer, and which is then placed in the mouth, over the maxillary anterior incisors 10.

In the event that the posterior teeth 11 come into contact before the lower incisors 9 contact the dome 13 while the semi-custom discluder 12 is in place, extension tabs 14 can be adhered to the dome 13 by the wearer until such time that the lower incisors 9 contact the dome-with-tab complex 17 before the posterior teeth 11 contact.

Other applications, variations and ramifications of this invention will occur to those skilled in the art upon reading this disclosure. Those are intended to be included within the scope of this invention, as defined in the appended claims.

I claim:

1. An interoral semi-custom discluding device which comprises:

a trough shaped to extend over at least a portion of the anterior and posterior surfaces of the anterior maxillary incisors in a spaced relationship therewith;

a soft material curable to a flexible, shape-retaining, state for filling said space between said trough and anterior maxillary incisors;

a dome on said trough extending distally when said trough is in place adjacent to said anterior maxillary incisors; and said dome having a surface configured to engage at least one lower anterior incisor prior to any contact between upper and lower posterior teeth while substantially avoiding lateral pressure on said at least one lower anterior incisor.

2. The interoral semi-custom discluding device according to claim 1 further including at least one thin, generally flat, tab for bonding to said dome surface for assuring that said contact between upper and lower posterior teeth is avoided.

3. The interoral semi-custom discluding device according to claim 1 wherein said curable soft material is a silicone resin for substantially filling said trough to support said anterior maxillary incisors.

\* \* \* \* \*